US006645529B2

(12) United States Patent
Gergely et al.

(10) Patent No.: US 6,645,529 B2
(45) Date of Patent: Nov. 11, 2003

(54) INSTANT GRANULES AND PROCESS FOR THEIR FORMULATION

(75) Inventors: Gerhard Gergely, Vienna (AT); Irmgard Gergely, Vienna (AT)

(73) Assignee: Dr. Gergely & Co., Vienna (AT)

( * ) Notice: Subject to any disclaimer, the term of this patent is extended or adjusted under 35 U.S.C. 154(b) by 0 days.

(21) Appl. No.: 09/857,459

(22) PCT Filed: Jan. 8, 2001

(86) PCT No.: PCT/EP01/00096

§ 371 (c)(1),
(2), (4) Date: Jun. 5, 2001

(87) PCT Pub. No.: WO01/51026

PCT Pub. Date: Jul. 19, 2001

(65) Prior Publication Data

US 2002/0168386 A1 Nov. 14, 2002

(30) Foreign Application Priority Data

Jan. 10, 2000 (CH) .............................................. 0033/00
Feb. 1, 2000 (EP) ............................................. 00101924

(51) Int. Cl.⁷ ............................ A61K 9/16; A61K 9/14; A61K 9/50; A61K 9/00
(52) U.S. Cl. ...................... 424/490; 424/489; 424/493; 424/497; 424/400
(58) Field of Search ................................ 424/489, 490, 424/493, 497, 400

(56) References Cited

U.S. PATENT DOCUMENTS 4,638,013 A * 1/1987 Moja et al. ................. 514/561
4,888,177 A * 12/1989 Gergely et al.
5,427,800 A * 6/1995 Cingotti
5,455,049 A 10/1995 Anaebonam et al. ....... 424/499
6,096,343 A * 8/2000 Gergely et al.

FOREIGN PATENT DOCUMENTS

| DE | 2618100 | | 11/1977 |
| EP | 0232277 | | 8/1987 |
| WO | 86/02834 | * | 5/1986 |

OTHER PUBLICATIONS

International Search Report dated Nov. 29, 2001.

* cited by examiner

*Primary Examiner*—Thurman K. Page
*Assistant Examiner*—Humera N. Sheikh
(74) *Attorney, Agent, or Firm*—Ostrolenk, Faber, Gerb & Soffen, LLP

(57) ABSTRACT

The pharmaceutical formulation according to the invention is in the form of instant granules, in which the surface of the particles of at least two different soluble carrier materials is covered or coated with at least one layer which contains -of from 50 to 120, preferably from about 60 to about 100, parts by weight of active substance per 100 parts by weight of carrier material -of at least one, preferably insoluble or slightly soluble, active substance, such as amino acids or antioxidants. A first carrier material constitutes from about 50 to about 80% by weight of the total carrier material and is selected from carrier materials having a bulk density of between 58 and 100, preferably between 63 and 90 g/100 ml, while the second carrier material is selected from carrier materials having a bulk density of between 30 to 55, preferably between 33 and 50 g/100 ml.

28 Claims, No Drawings

INSTANT GRANULES AND PROCESS FOR THEIR FORMULATION

This application is a 371 of PCT/EP01/00096 filed Jan. 8, 2001.

The invention relates to a pharmaceutical formulation in the form of instant granules according to the precharacterizing clause of claim 1. Such a formulation is described, for example, in EP-B1-232,277. Said publication discusses the fact that, according to the invention, an amino acid (e.g. tryptophane in Example 1) can be processed as an active substance or a plurality of active substances (e.g. vitamins and mineral salts in Example 2, applied to a carrier material comprising acid, which presents a problem for kidney patients) can be processed, it also being stated that a plurality of layers can be applied to the granular carrier material of soluble carbohydrate by means of a binder solution, for anchoring relatively large amounts of active substance.

This last proposal is subject to limits in practice, especially in the case of amino acids, unless special measures are taken. In particular, it has been found that, for amounts of active substance which are greater than the amounts occurring in the examples mentioned in EP-B1-232,277 and for active substances which are very bulky, the active substances on the carbohydrate carriers cannot be sufficiently anchored by the binder layer alone and too much active substance remains free, with the result that neither the desired suspension property nor the flowability of the product can be satisfactorily achieved.

In the case of amounts of active substance of from 60 to 100 parts by weight—based on 100 parts by weight of carrier—undesired agglomerations of the active substance occur when the binder is applied repeatedly, so that, on introduction into water, the desired suspension is no longer achievable and the particles sink to the bottom or remain on the surface of the water.

It is therefore one object of the invention to improve the formulation described in EP-B1-232,277 and its preparation in such a way that instant granules and a process for their preparation are provided, by means of which it is possible easily to accommodate even very large amounts of even different—in particular insoluble or slightly soluble—active substances, in particular a plurality of amino acids, analgesics, antioxidants, such as, for example, paracetamol, beta-carotene, etc, After introduction into water, the pharmaceutical formulation should be suspended within an appropriately short time by stirring, should have a pleasant taste and should furthermore remain in suspension for an appropriately long time.

This requirement is particularly applicable to amino acids because they have to be administered in large amounts per dose, both when used as a food supplement and particularly as a preparation for kidney patients who have to survive on a low protein diet and require a large supply of amino acids. By supplying essential amino acids, the deficit can be satisfactorily compensated, with the result that adverse symptoms can be prevented and the necessity of a dialysis can in certain circumstances be postponed.

There are on the market a number of amino acid-containing products with essential amino acids in tablet or capsule form, but, for example, kidney patients have to take 5 units of these, 3 times a day, which presents considerable problems for the patient or consumer, all the more so since this group of—mostly elderly—patients usually also has to take a number of other medicaments, generally in tablet form. A dosage form which can be administered in liquid form in order to facilitate the intake for the patient was therefore desirable for this amino acid medication.

A further object of the invention was therefore to develop an instant formulation comprising a high dose of active substance and small amounts of excipients, which formulation can be readily suspended in a small amount of water, say from 50 to 100 ml, and is readily accepted by the patient with regard to taste. Consequently, consumption by the patient should be substantially facilitated.

The difficulty of developing such a product which is suspendable in water was associated with the weight ratios and volume ratios of carrier material to active substance. Granulation of the active substances alone did not achieve the object since this resulted, on the one hand, in agglomerates of the active substances which did not disintegrate into their individual particles within the distribution time in water, therefore were insufficiently suspendable and sank to the bottom of the glass, on the other hand the active substance partially did not granulate at all and was therefore floating to the surface and no proper suspension could be achieved (see negative Example 1).

A similar, slightly better, effect occurred when excipients were granulated together with the active substances, since in this case, on the one hand, the addition of solution caused the easily soluble carrier materials to agglomerate and, in another case, the resulting granulation of the particles of active substance was insufficient for achieving a flowable product (see also negative example 2).

The application of a phospholipid (Epikuron®) solution as a surfactant to the granulated active substances well as to excipients granulated together improved the suspension of the active substances, but coarser particles still remained in the suspension and a part of the active compound was still floating to the surface (see negative examples 1a and 2a).

When a corresponding amount of binder was added to the solution, the result was an undesired coarse-particle agglomeration of the active substances and/or of the active substances with the carrier material, which, in spite of milling to the desired particle size, exhibited reduced suspension properties and settled on the bottom when stirred into water.

All these problems have been overcome according to the invention by anchoring only a part of the active substances on a first, preferably compact and/or crystalline, carrier material having a bulk density of between 58 and 100, preferably between 60 and 95 g/100 ml, while the excess of the active substances not anchored to the surface of the first carrier material is granulated by means of the introduction of a second, voluminous, e.g. spray dried, carrier material which is selected from carrier materials having a bulk density of between 30 to 55, preferably between 33 and 50 g/100 ml and thereby are usually more easily and/or quickly soluble than the first carrier material. Preferred carrier materials are listed in Table 1.

The bulk density of conventional products available on the market is not directly depending on the grain size distribution which may widely differ.

Advantageous embodiments, further developments and improvements of the invention are described in the dependent claims.

TABLE 1

| | bulk | grain size distribution of conventional products | |
|---|---|---|---|
| | density | >0.5 mm | 0.2– |

| carrier material | (g/100 ml) | (% by weight) | 0.5 mm (% by weight) | <0.2 mm (% by weight) |
|---|---|---|---|---|
| First carrier materials | | | | |
| sorbitol | 58 | 0 | 58 | 42 |
| mannitol | 63 | 0 | 92 | 8 |
| lactose | 69 | 0 | 36 | 64 |
| saccharose (fine grain) | 81 | 0 | 71 | 29 |
| saccharose (coarse grain) | 88 | 28 | 68 | 4 |
| hydrogenated maltose | 90 | 99 | 1 | 0 |
| trisodiumcitrate.2H$_2$O | 95 | 22 | 70 | 8 |
| monocalcium phosphate.H$_2$O | 82 | 0 | 8 | 92 |
| second carrier materials | | | | |
| maltodextrine (spray-dried or-granulated) | 33 | 16 | 39 | 45 |
| sorbitol (spray dried) | 45 | 19 | 77 | 4 |
| mannitol (spray dried) | 45 | 0 | 20 | 80 |
| glucose syrup (dried) | 50 | 0 | 3 | 97 |
| instant sugar | 50 | 9 | 36 | 55 |

This invention was based on the consideration that, in cases where small amounts of excipients are desired, either on the basis of dietary or medical indication or for economic reasons, it is necessary to find a procedure which makes it possible to combine bulky insoluble or slightly soluble active substances in a weight ratio of from 60 to 100 parts by weight—with 100 parts by weight of the total carrier material.

This is possible by introducing the carriers in two or more stages. In the first step, a part of the total carrier materials—consisting of at least 80, preferably at least 100% by weight of the first carrier material—is initially taken; the surface is then wet by adding water, ethanol, an ethanol/water mixture and/or a binder solution. Thereafter, the active substances are added and are at least partly anchored to the surface of the carrier particles. In a second step, by introducing a further carrier material and by partially dissolving its surface by means of the residual moisture present in the material—or if required with the addition of further water, ethanol, an ethanol/water mixture or a binder solution—the remaining, still unanchored particles of active substance are, at least partially, anchored thereon and/or are granulated with the second carrier material. This step can—if required—be repeated.

In practice, it has been found that the best results are obtained with an amount of liquid of from 1 to 10, preferably of about 3 to about 7 parts by weight (based on 100 parts by weight of carrier material and active substance). The lower limit is applicable when using pure water and substantially insoluble or very slightly soluble active substances; an average value is to be assumed in the case of ethanol or ethanol/water mixtures and also sparingly soluble active substances; the upper limit is applicable when a binder solution is used, especially if the carrier particles and the active substances are less susceptible to agglomeration.

It has furthermore proved expedient if initially only from 10 to 25, in particular from 15 to 20, % by weight of the intended total amount of liquid are used for wetting the first carrier material. This should in fact be essentially moistened but only minimally superficially dissolved since otherwise the carrier material has the tendency to agglomerate itself, with the result that uniform distribution, namely uniform application of the active substance to the individual carrier crystals, becomes more difficult.

The remaining amount of liquid is then used for wetting the remaining active substance and the second carrier material. In many cases, it has proved expedient for the same reason, namely for the avoidance of agglomeration of the carrier material, to distribute the remaining amount of liquid over the first carrier material already covered with particles of active substance and over the free particles of active substance before the addition of the second carrier material. Depending on the type of ingredients and on the procedure, articles of the second carrier material coated analogously with active substance and/or particles granulated with active substance and carrier material are then obtained.

It is then possible to proceed as follows for a formulation in which free-flowing, suspendable granules are to be obtained from 70 to 80 parts by weight of bulky, insoluble or slightly soluble active substances on 100 parts b weight of carrier:

In the first step, from 60 to 80% of particles of the first carrier material are wet with, for example, a binder solution. The binder solution may be an ethanolic or an ethanol/water solution of at least one of the following substances: sugar, sugar alcohol, maltodextrin, polyvinylpyrrolidon or other hydrocolloids. In some cases it is preferable to slightly wet the particles of the first carrier material with ethanol or with an ethanol/water-mixture 70:30 before applying the binder solution in order to avoid an undesired agglomeration of said particles.

Thereafter, at least a part—preferably the major part—of the active substances is added and at least partially anchored on the surface of the carrier particles. Optionally, the remainder of—or some additional—liquid is added, and the remaining particles of active substance are wet by means of said additional binder solution and fixed to the existing particles of the first carrier material—which are already covered by a part of the active substance—and/or to one another. In case the surface of the first carrier material and/or of the active substances is too much dissolved, it might be advantageous to partially dry the mixture before or during the addition of the remaining part of said liquid, of particles of the second carrier material, and/or of any remaining part of the active substances.

This is followed, in a second step, by the addition of the second carrier material. For example spray-dried, spray granulated or agglomerated materials, for example sugar alcohols, such as sorbitol, xylitol or mannitol; instant sugar (i.e. spray dried saccharose), and further hydrolyzed starch products such as maltodextrin, soluble corn syrup solids or starch sugar (e.g. dried glucose syrup), are suitable for this purpose owing to their bulk density, the fluffy, bulky structure an the good surface dissolution capability. If maltodextrin is used as a second carrier material, a particle size distribution of 20–25%>0.4 mm, 35–65%<0.4 mm>0.1 mm and a maximum fraction of 20–35%<0.1 mm is advisable. Naturally the above specified second carrier materials may also be supplied by other processes, besides spray drying and spray granulating, provided that the carrier materials are obtained within the appropriate bulk density.

Because of the moisture already present in the material or, if required, optionally an additionally introduced one, the surface of the second carrier particles now also partially dissolves and the still free active substances are anchored thereon; on the other hand, the second carrier particles serve as a core for granulation of the still not anchored active substances, with the advantage that, upon the introduction to water, the core quickly dissolves, the particles of active substance are released and hence a good suspension is permitted. The carrier materials can also be introduced in a plurality of steps. Would the second carrier material be introduced at an earlier stage—when there are no amino acids acting as a buffer yet—agglomeration of the carrier particles would occur before the active substances could be anchored on the carrier particles' surface.

Compact, for example, sorbitol or mannitol can be used as the first carrier material. In the case of such sugar alcohols, an excessively large dust fraction should be avoided in order to prevent agglomeration of the carriers on moistening by partial dissolution of the fine fractions; preferably, a maximum of only 5% of the carrier particles are smaller than 0.1 m. They may be present both in crystalline form and as spray-dried or granulated raw material. Furthermore, sucrose having the following particle size distribution may also be used as carrier material:
<0.5 mm>0.3 mm: 0–60% by weight
<0.3 mm>0.1 mm: 10–85% (the main sieve fraction)
<0.1 mm: 0–15%

For amino acids following particle size distributions may be applicable: In the group of L-isoleucine, L-leucine and L-valine, a maximum of 15% by weight should be >0.3 mm, 70–95% by weight should be between 0.1 and 0.3 mm, and 1–20% by weight should be <0.1 mm. In the group of L-phenylalanine, L-histidine, L-methionine, L-threonine, L-tryptophane and L-tyrosine, a maximum of 5% by weight should be >0.3 mm, 30–90% by weight should be between 0.1 and 0.3 mm, and 5–60% by weight should be <0.1 mm. In L-lysinacetate, 5–30% by weight should be >0.3 mm, 30–70% by weight should be between 0.1 and 0.3 mm, and a maximum of 25% by weight should be <0.1 mm.

For β-carotene or DL-α-tocopherolacetate, a maximum of 15% by weight should be >0.3 mm, 70 to 95% by weight of the particle size distribution should be between 0.1 and 0.3 mm, and a maximum of 30% by weight should be <0.1 mm.

To achieve an improvement in the suspension, taste improving and/or suspension aids, such as $Ca(H_2PO_4)_2 \cdot H_2O$ or trisodiumcitrate·$2H_2O$. Both and other soluble alkaline salts of edible organic acids can also act as carrier materials. For instance, trisodiumcitrate·$2H_2O$ together with further carrier materials my be used as first carrier. Wetting agents may also be used, too. Both anionic surfactants, such as sodium laurylsulphate or dioctyl sulphosuccinate, and sugar esters, phospholipids, polysorbates or hydrogenated castor oils are suitable for this purpose.

For improving the taste, artificial sweeteners and flavors, or acids or their acidic salts, in the allowed amount or amount permitted for the patient group, and also vitamins may be added to the formulation.

It is thus possible, according to the invention, to combine vitamins—such as ascorbic acid, B-vitamins, folic acid, biotin, calcium pantothenate, as well as fat soluble ones such as tocopherol, retinol and cholecalciferol (vitamins A, D and E)—and also, if required, trace elements such as selenium, chromium, manganese, molybdenum, zinc, iron and minerals such as magnesium and calcium—with the active substance, for example amino acids.

Accordingly, it is also possible to apply at least one antioxidant and/or vitamin as the active substance together with trace elements such as selenium, chromium, manganese, molybdenum, zinc, iron and/or minerals such as magnesium and calcium.

A particular formulation is an amino acid instant formulation for kidney patients. For medical reasons, special attention must be paid to the composition of the formulation in this case. For example, a dose which is administered three times a day should contain as little sugar as possible, and mannitol or sorbitol in an amount of not more than 1.5 g, and furthermore as small an amount as is possible of organic acids, such as citric acid or tartaric acid or their acidic salts. Phosphate-containing excipients are also undesirable.

The essential amino acids, i.e. L-valine, L-isoleucine, L-tyrosine, L-threonine, L-methionine, L-leucine and L-lysine, should be present in a corresponding amount per dose, the addition of some further amino acids being expedient, such as, in particular, L-histidine, L-tryptophane, L-phenylalanine and arginine aspartate. If the daily requirement is distributed over three doses, for example, 450 mg of L-leucine, 675 mg of L-valine, 300 mg of L-isoleucine, 325 mg of L-histidine, 375 mg of L-tyrosine, 125 mg of L-tryptophane, 325 mg of L-threonine, 40 mg of L-methionine, 350 mg of L-phenylalanine and 480 mg of L-lysine acetate per dose have proved expedient.

Instant granules according to the invention and containing said doses can be readily suspended in 50 to 100 ml of water and—together with sweeteners and flavors—are pleasant to drink. Since kidney patients are limited in their liquid intake, it was necessary to solve the problem of developing an instant product which has sufficiently good suspension properties in a very small amount of solution, it being necessary for the amount of water per dose as far as possible not to exceed 100 ml. The product can also be suspended in 50 ml of water but the stability of the suspension is better with a larger amount of water, so that dissolution in 75 ml of water is recommended.

To check the stability of the suspension as a function of the amount of water, experiments were carried out to determine how much of the amino acids settle out per unit time. One pouch each of the product according to example 1 below was introduced into 50 ml, 75 ml and 100 ml resp. of water, stirring was carried out for 20 sec and the sediment was measured after 1 to 15 min. The vessel used was a 100 ml measuring cylinder having a diameter of 25 mm. The results are given in the following Table 2:

TABLE 2

| Minutes after stirring | 50 ml of water height of suspension 103 mm sediment in mm | 75 ml of water height of suspension 148 mm sediment in mm | 100 ml of water height of suspension 195 mm sediment in mm |
|---|---|---|---|
| 1 | 1 | traces | traces |
| 2 | 2 | 1 | 1 |
| 5 | 2 | 2 | 1 |
| 10 | 2 | 3 | 2 |
| 15 | 3 | 3 | 2 |

It was found that the suspension is very stable and only small differences were observed in an amount of 50 ml and 75 ml of water. The product exhibited slightly better behavior on dissolution in 100 ml of water. If the product is stirred into 50 ml and 100 ml of water in a glass, a slight sediment forms after one minute and no longer increases measurably after 20 to 25 minutes, and only the suspension becomes very slightly flaky.

These advantages—from a technical point of view and in terms of taste—could only be achieved by means of the formulation and by the process for its preparation according to the invention based on the consideration that it is necessary to proceed in two stages—on the one hand owing to the preferred, large amounts of active substance(s) and, on the other hand, also because of any use of carrier materials which are in fact particularly easily and rapidly soluble, such as, for example, spray dried or spray granulated sorbitol, xylitol, mannitol, maltodextrin, instant sugar and glucose syrup. Under certain circumstances, it may then even be expedient in any case to use the second binder solution based on ethanol or at best on an ethanol/water mixture, if further amounts of active substance are to be applied.

It was necessary to choose the composition and the process in such a way that agglomeration of the carrier substances could be prevented, in order to provide as large a surface as possible for the application of the active substances and, on the other hand, to wet and to partially dissolve the surface so well that a large part of the amino acids could be applied to the carrier surface. This could be achieved by the choice of the ingredients and by a composition according to the invention.

Furthermore, the acid components—in the formulation which contains sucrose—were not mixed with the carrier substances and wet, in order to prevent inversion of the sugar and hence undesired sticking together of the carrier materials due to the increased adhesiveness of the invert sugar. Consequently, the acidic components and the soluble lysine acetate were not added until shortly before the final drying, when only little moisture and adhesiveness of the granules were present, with the result that it was also possible to obtain a more stable product.

EXAMPLE 1

930 g of fine mannitol granules, 823 g of finely crystalline sugar and 18 g of sodium chloride are introduced, optionally with artificial sweeteners, into a mixing vessel, preferably a vacuum vessel, and are heated to 60° C. with mixing. Thereafter, a vacuum is applied and 22 ml of 96% ethanol are aspirated and distributed. A solution of 5.5 ml of 96% ethanol, 5.5 ml of water, 6 g of sugar and 0.4 g of citric acid is then aspirated and distributed; then 1965 g of a mixture of the desired amino acids are added.

Thereafter, 180 ml (=208.4 g) of the same solution which contains 133 ml of water, 71 g of sugar and 4.4 g of citric acid are aspirated, preferably in vacuum, the solution is distributed and 900 g of maltodextrin are then mixed in. The maltodextrin superficially dissolves as a result of the moisture now present in the material and binds the free particles of active substance. 160 ml of a solution which consists of 135 ml of ethanol and 21 g of Epikurone® (phospholipids) are then aspirated and are distributed in the material. Finally, 246 g of a citric acid/tartaric acid mixture and optionally 288 g of a further, for example coarse-particled, soluble amino acid, such as, for example, L-lysine acetate, 30 g of rice starch and 48 g of a lemon flavor are also introduced. After the final drying, the granules are sieved to 1.2 mm.

As a result of this procedure, instant granules are obtained which contain an amount of 3.75 g of amino acids per dose of 8.94 g, are readily suspendable in 75 ml of water and have a good taste.

If samples of one such dose (the contents of one pouch, e.g. a sachet) are stirred in 75 ml water of 17° C. for 30 sec. and the grain size of the suspended particles is determined, thereafter. The grain size distribution of the suspended particles could be described as follows: 80 to 100% by weight <0.3 mm, 40 to 60% by weight <0.09 mm, and 5 to 20% by weight <0.01 mm.

EXAMPLE 2

Sugar-Free Formulation 1750 g of fine mannitol granules and 18 g of sodium chloride are introduced, optionally with artificial sweeteners, into a mixing vessel, preferably a vacuum vessel, and are heated to 60° C. with mixing. Thereafter, a vacuum and 40 ml of a solution of 27 ml of water, 18 g of sorbitol and 1.1 g of citric acid are aspirated and distributed; then 1965 g of a mixture of the desired amino acids are added.

Thereafter, 220 ml of the same solution (containing 145 ml of water, 98 g of sorbitol and 5.4 g of citric acid) are aspirated, preferably in vacuum; the solution is distributed and then 800 g of spray-dried sorbitol are mixed in. As a result of the moisture present in the material, the sorbitol dissolves superficially and binds the free particles of active substance. 160 ml of a solution which consists of 130 ml of ethanol and 21 g of Epikuron® (phospholipid) are then aspirated and distributed in the material. Finally, 245 g of a citric acid/tartaric acid mixture and optionally 288 g of a further, for example coarse-particled soluble amino acid, such as, for example, lysine acetate, and 48 of lemon flavor are also introduced. After the final drying, the granules are sieved to 1.2 mm.

As a result of this procedure, sugar-free instant granules are obtained which contain an amount of 3.75 g of amino acids per dose of 8.85 g, are readily suspendable in 75 ml of water and have a good taste.

The amino acid products corresponding to Examples 1 and 2 cannot only be administered as a suspension in water but also be stirred into soft drinks or orange juice or be added to dairy products. Depending on administration, the product can also be added, without flavor and sweetener, to various drinks, such as even to milk and milk drinks.

EXAMPLE 3

Antioxidants 500 parts by weight of fine sucrose granules, 866 parts by weight of spray-dried mannitol and 12 parts by weight of saccharin are heated to 60° C. with mixing. These carrier materials are wet with 30 ml of water. The active substances, consisting of 1000 parts by weight of 50% vitamin E dry powder and 120 parts by weight of 10% beta-carotene (bulk density 70 g/100 ml), are then introduced. A solution of 50 parts by weight of sorbitol in 100 parts by weight of ethanol is distributed thereon and 500 parts by weight of instant sugar are then introduced. The product is dried and mixed with granules consisting of 100 parts by weight of citric acid, 150 parts by weight of vitamin C, 25 parts by weight of sodium carbonate and a desired amount of flavor.

The finished product comprises 65 parts by weight of active substance and 100 parts by weight of carrier, and gives a pleasant-tasting formulation which is readily suspendable in water.

A simple mixture of the active substance or substances with the excipients did not give a satisfactory result since, on the one hand, the required content uniformity of the active substance per dose could not be achieved and, on the other hand, the product did not exhibit sufficient flowability to enable it to be filled into pouches as a single dose. Furthermore, the amino acids do not readily suspend in water but agglomerate and stay on the surface of the liquid.

Granulation was therefore necessary in order to eliminate the problems mentioned and to obtain a preparation which can be easily metered for the patient's requirements and which permits uniform dosage of the active substances.

For example, if the components of Example 1 were only mixed, the mixture had a bulk density of 55 g per 100 ml and is non-flowable, while a granulated product prepared according to the invention has a bulk density of 6–70 g per 100 ml; it can well and uniformly be metered on conventional filling lines.

EXAMPLE 4

475 g of trisodium citrate dihydrate, 1170 g of free-flowing sugar, 90 g of primary calcium phosphate monohydrate and 50 g of sodium chloride, optionally with artificial sweeteners, are introduced into a mixing vessel, preferably a vacuum vessel, and heated to 60° C. while mixing. Thereafter, a vacuum is applied and 182 ml (=210 g) of a solution of 125 ml of water, 80 g of sugar and 5 g of citric acid are aspirated, said solution is distributed and 800 g of L-leucine, 400 g of L-valine and 400 g of L-isoleucine are then added.

850 g of spray-dried maltodextrin are then mixed in. The maltodextrin partially dissolves as a result of the moisture now present in the material and binds the exposed particles of active substance. 225 ml of a solution which consists of 185 ml of ethanol and 25 g of Epikuron® (phospholipids) are then aspirated and are distributed in the material. Finally, 950 g of citric acid and optionally 900 g of a further, for example soluble amino acid, such as, for example, arginine aspartate, 50 g of rice starch, 4.2 g of 33% vitamin B6 and 50 g of a lemon flavor are also introduced. After the final drying, the granules are sieved to 1.2 mm.

By means of this procedure, instant granules which contain an amount of 2.5 g of amino acids per dose of 6.34 g, are readily suspendable in 75 ml of water and have a good taste are obtained.

EXAMPLE 5

Dissolving Times of Different Carrier Materials

Testing conditions: 10 g of each carrier material was added to 100 ml water of 17° C. in a 400 ml beaker and stirred at 500 rpm by a magnetic stirrer. Dissolution was determined visually. Respective dissolving times are shown in Table 3.

TABLE 3

| Carrier | Bulk density in g/100 ml | Dissolving time in sec |
|---|---|---|
| First carrier material | | |
| sorbitol | 58 | 90 |
| mannitol (fine granulated) | 62 | 95 |
| hydrogenated maltose | 90 | 200 |
| lactose | 69 | 120 |
| trisodiumcitrat.2H$_2$O | 95 | 85 |
| Second carrier materials | | |
| maltodextrin (spray dried or granulated) | 33 | 55 |
| sorbitol (spray dried) | 45 | 50 |
| mannitol (spray dried) | 45 | 55 |
| dried glucose syrup | 50 | 45 |
| instant sugar (spray dried saccharose) | 45 | 15 |

NEGATIVE EXAMPLE 1

Granulation of the Amino Acids Alone

A mixture of 1965 g of the amino acids was prepared and the mixture was heated to 60° C. while mixing. Thereafter, 200 ml of a solution containing 133 ml of water, 89 g of sucrose and 9.6 g of citric acid were added and the solution was distributed while stirring. Finally, the granules were dried.

On introduction of the granules into water, it was found that scarcely any granulation could be achieved with this amount of solution and the amino acids for the most part remain at the surface of the water and on the glass and virtually no suspension of the amino acids could be obtained.

NEGATIVE EXAMPLE 1a

The experiment of negative example 1 was then repeated with twice the amount of solution, i.e. 400 ml.

Result:

Nonuniform granulation of the amino acids was found, with the result that, on introduction into water, a portion remained at the surface and at the rim of the glass, a portion had sunk to the bottom and a portion floated in the water in very coarse flocks, a part of which was forced to the surface and the other part sank to the bottom. In practice, however, a roughly uniform suspension did not form.

On the basis of this result, an Epikuron® solution as in Example 1 (150 ml of ethanol and 21 g of Epikuron® [phospholipid]) was applied to the granules. On introduction into water, a situation similar to that in the experiment without Epikuron® was encountered but a suspension containing particles, some of which were coarser, was formed, but the flocculent agglomerations of the amino acids were no longer present. The advantageous effect of the suspension aids on the suspension behavior was evident.

NEGATIVE EXAMPLE 2

Carrier and Amino Acids Granulated Together 930 g of fine mannitol granules, 793 g of finely crystalline sugar, 18 g of sodium chloride and 900 g of maltodextrin, optionally with artificial sweeteners, and 1965 g of a mixture of the desired amino acids and furthermore 245 g of citric acid/tartaric acid mixture and optionally 288 g of a further, for example coarse-particled, soluble amino acid, such as, for example, lysine acetate, are introduced into a mixing vessel, preferably a vacuum vessel, and heated to 60° C. while mixing.

Thereafter, 400 ml of a solution containing 288 ml of water, 153.6 g of sucrose and 9.6 g of citric acid are aspirated—preferably in vacuum—and the solution is distributed. After the final drying, the granules are sieved to 1.2 mm.

Result:

As for Negative Example 1a, but a portion of the amino acids was suspended.

NEGATIVE EXAMPLE 2a

Negative example 2, was repeated with application of a solution of 150 ml of ethanol and 21 g of Epikuron®, too.

On introduction into water and after stirring for 20 seconds, an amino acid foam layer formed on the surface, a portion sank to the bottom and some of the amino acids were suspended, coarser particles being observable in the suspension.

The sedimentation rate have been also measured but, since a portion of the amino acids remained at the surface, the amount of sedimentation is also certainly not very informative owing to the different structure of the particles.

Experiments were carried out to determine how much of the amino acids settle out per unit time. One pouch each of the product according was introduced into 50 ml, 75 ml, and 100 ml resp. of water, stirring was carried out for 20 sec and the sediment was measured after 1 to 15 min. The vessel used was a 100 ml measuring cylinder having a diameter of 25 mm. The results are shown in Table 4.

TABLE 4

| Minutes after stirring | 50 ml of water height of suspension 104 mm sediment in mm | 75 ml of water height of suspension 147 mm sediment in mm | 100 ml of water height of suspension 187 mm sediment in mm |
|---|---|---|---|
| 1 | 2 | 1 | 1 |
| 2 | 2 | 1 | 2 |
| 5 | 3 | 2 | 2 |
| 10 | 4 | 3 | 2 |
| 15 | 4 | 3 | 2 |

What is claimed is:

1. Pharmaceutical formulation in the form of granules capable of suspension in water, in which the surface of the particles of at least two different soluble carrier materials is covered or coated with at least one layer which contains at least one active substance, characterized in that said active substance is present in solid pulverized form, and wherein some of said active substance is attached by a binder to a first carrier material that is selected from carrier materials having a bulk density of between 58 and 100, and wherein some of said active substance is attached to a tacky layer of a second carrier material that is selected from carrier materials having a bulk density of between 30 to 55.

2. Formulation according to claim 1, characterized in that the first carrier material is selected from the group consisting of sugar alcohols, saccharose, hydrogenated maltose, lactose and soluble alkaline salts of edible organic acids, and the second carrier material is selected from the group consisting of sugar alcohols, hydrolyzed starch products and instant sugar.

3. Formulation according to claim 2, characterized in that for the first carrier material the sugar alcohols are selected from the group consisting of sorbitol and mannitol, and for the second carrier material the sugar alcohols are selected from the group consisting of sorbitol, mannitol and xylitol, while the hydrolyzed starch products are selected from the group consisting of maltodextrine, soluble corn syrup solids and starch sugar.

4. Formulation according to claim 1, characterized in that the particles of the first carrier material constitute from 50 to 80% by weight of the total carrier material, and a total of from 50 to 120 parts by weight of active substance are present per 100 parts by weight of carrier material.

5. Formulation according to claim 1, characterized in that in the particular size distribution of any active substance selected from the group consisting of L-isoleucine, L-leucine and L-valine, or of the total amount of such active substances, a maximum of 15% by weight should be >0.3 mm, 70 to 95% by weight should be between 0.1 and 0.3 mm, and 1 to 20% by weight should be <0.1 mm.

6. Formulation according to claim 1, characterized in that in the particle size distribution of any active substance or of the total amount of active substances selected from the group consisting of L-phenylalanine, L-histidine, L-methionine, L-threonine, L-tryptophane and L-tyrosine, a maximum of 5% by weight should be >0.3 mm, 30 to 90% by weight should be between 0.1 and 0.3 mm, and 5 to 60% by weight should be <0.1 mm.

7. Formulation according to claim 1, characterized in that in the particle size distribution of L-lysinacetate: 5 to 30% by weight should be >0.3 mm, 30 to 70% by weight should be between 0.1 and 0.3 mm, and a maximum of 25% by weight should be <0.1 mm.

8. Formulation according to claim 1, characterized in that the bulk density and the amounts of the carrier materials of the grain size and the amounts of active substances are selected such that a dose of between 8 and 9 g of the formulation suspended in 75 ml water maintains at least 80% by weight of the formulation in suspension during 10 minutes.

9. Formulation according to claim 1, characterized in that at least one amino acid, selected from the group consisting of L-valine, L-isoleucine, L-tyro sine, L-threonine, L-methionine, L-lysine or a salt thereof, L-leucine, L-histidine, L-tryptophane, L-phenylalanine, arginine aspartate, or a mixture thereof is present as active substance.

10. Formulation according to claim 9, characterized in that a mixture is present in sachets in an amount such that
    1800–2700 mg of L-valine;
    750–1200 mg of L-isoleucine;
    1000–1500 mg of L-tyrosine;
    800–1300 mg of L-threonine;
    1200–1800 mg of L-methionine;
    800–1500 mg of L-lysine acetate, are contained in from one to three doses per day.

11. Formulation according to claim 10, characterized in that the grain size of the suspended particles of 80–90% by weight is smaller than 0.3 mm, of 40–60% by weight is smaller than 0.09 mm and of 5–20% by weight is smaller than 0.01 mm, after the content of a sachet has been stirred in 75 ml water of 17° C. for 30 sec.

12. Formulation according to claim 1, characterized in that it further contains at least one substance from the group consisting of edible organic acid, at least one salt of an edible organic acid, surfactant, emulsifier, sweetener, flavor, taste masking compounds and suspension aid(s).

13. Formulation according to claim 1, characterized in that at least one compound selected from the group consisting of antioxidants; and a mineral; is present as active substance.

14. Formulation according to claim 13, characterized in that at least one antioxidant selected from the group consisting of n-carotene, ascorbic acid or DL-α-tocopherolacetate is present.

15. Formulation according to claim 14, characterized in that at least one antioxidant is present together with at least one trace element selected from the group consisting of selenium, chromium, manganese, molybdenum, zinc, and iron; and/or at least one mineral selected from the group consisting of magnesium and calcium.

16. Process for the preparation of instant granules according to claim 1, comprising the steps of (i) wetting and mixing particles of a first carrier material with at least a part of the intended total amount of at least one liquid selected from the group consisting of water, ethanol, a binder solution and a mixture of any of the foregoing, (ii) coating the wet (particles of step (i) by adding at least a part of a granular or pulverulent active substance (iii) adding any remaining part of said liquid of step (i), (iv) adding particles of a second carrier material, and (v) drying and finally milling and/or sieving to the desired particle size, wherein drying is carried out in a vacuum mixer.

17. Process according to claim 16, wherein said liquid is applied in a total amount of from 1 to 10% by weight of the total weight of carrier materials and active substances.

18. Process according to claim 16, wherein before or during the process steps (ii) through (iv) the mixture is partially dried.

19. Process according to claim 16, wherein from 60 to 80% by weight of the total carrier material—consisting of at least 80% by weight o the first carrier material—are wet with from 10 to 25% by weight—of said liquid, after which the following components are added one after the other while the mixture is in movement: (i) one or more active substances in an amount of from 50 to 120 parts by weight per 100 parts by weight of the total carrier material, (ii) the remaining amount of said liquid, (iii) the remainder of the carrier material and (iv) the remainder of the active substances.

20. Process for the preparation of a pharmaceutical formulation according to claim 1, characterized in that particles of a first carrier material are wet with at least a part of the intended total amount of a liquid selected from the group consisting of water, ethanol, ethanol/water mixture or aqueous solution of a binder, after which the following components are added while the mixture is in movement:

(i) at least a part of the granular or pulverulent active substances, (ii) any remaining part of said liquid, (iii) particles of the second carrier material, whereafter the resulting mixture is only partially dried and then at least one of the following substances is added: edible organic acid, at least one salt of an edible organic acid surfactant, emulsifier, sweetener, flavor, taste and/or suspension aid(s) and further active substance(s), followed by final drying and milling and/or sieving to the desired particle size of the resulting granules.

21. Process according to claim 20, wherein further a surfactant is added after step (iii) and before the partial drying of the resulting mixture, wherein the surfactant and/or suspension aids are selected from the group consisting of sugar esters, phospholipids, polysorbates, hydrogenated castor oils and anionic surfactants.

22. Process according to claim 20, wherein the further active substances comprise substances which are easier soluble and/or of larger grain size than the first added ones, in particular L-lysine acetate and/or arginine aspartate.

23. Process according to claim 16, wherein at least one of the process steps is repeated at least once.

24. Formulation according to claim 1, wherein the first carrier material is selected from carrier materials having a bulk density of between 60 and 95 g/100 ml.

25. Formulation according to claim 1, wherein the second carrier material is selected from carrier materials having a bulk density of between 33 and 50 g/100 ml.

26. Formulation according to claim 4, wherein a total of 60 to 100 parts by weight of active substances are present per 100 parts by weight of carrier material.

27. Formulation according to claim 10, wherein the formulation further comprises at least one of the following amino acids:

1200–1800 mg of L-leucine; 600–1200 mg of L-histidine; 300–500 mg of L-tryptophane, and 900–1400 mg of L-phenylalanine.

28. Formulation according to claim 10, characterized in that the mixture comprises additionally at least one substance selected from the group consisting of 1200–1800 mg L-leucine, 600–1200 mg L-histidine, 300–500 mg L-tryptophane, and 900–1400 mg L-phenylalanine.

* * * * *